United States Patent
Barroso et al.

(10) Patent No.: US 10,064,255 B2
(45) Date of Patent: Aug. 28, 2018

(54) LIGHTING SYSTEM, PARTICULARLY FOR DELIRIUM REDUCTION IN INTENSIVE CARE UNITS

(71) Applicant: PHILIPS LIGHTING HOLDING B.V., Eindhoven (NL)

(72) Inventors: Andre Melon Barroso, Aachen (DE); Thomas Falck, Aachen (DE)

(73) Assignee: PHILIPS LIGHTING HOLDING B.V., Eindhoven (NL)

( * ) Notice: Subject to any disclaimer, the term of this patent is extended or adjusted under 35 U.S.C. 154(b) by 152 days.

(21) Appl. No.: 14/402,162

(22) PCT Filed: May 15, 2013

(86) PCT No.: PCT/IB2013/053945
§ 371 (c)(1),
(2) Date: Nov. 19, 2014

(87) PCT Pub. No.: WO2013/175348
PCT Pub. Date: Nov. 28, 2013

(65) Prior Publication Data
US 2015/0126806 A1    May 7, 2015

Related U.S. Application Data

(60) Provisional application No. 61/651,043, filed on May 24, 2012.

(51) Int. Cl.
*A61M 21/02* (2006.01)
*H05B 37/02* (2006.01)
*A61M 21/00* (2006.01)

(52) U.S. Cl.
CPC ......... *H05B 37/0227* (2013.01); *A61M 21/02* (2013.01); *H05B 37/029* (2013.01);
(Continued)

(58) Field of Classification Search
CPC ............ H05B 37/0218; H05B 37/0227; H05B 37/029; H05B 37/0245; H05B 37/0281;
(Continued)

(56) References Cited

U.S. PATENT DOCUMENTS

| 5,343,121 | A | 8/1994 | Terman et al. |
| 2004/0257237 | A1* | 12/2004 | Bialecki, Jr. ........ H05B 37/0227 340/686.1 |

(Continued)

FOREIGN PATENT DOCUMENTS

| CN | 101060735 A | 10/2007 |
| CN | 101678209 A | 3/2010 |

(Continued)

OTHER PUBLICATIONS

Wilson, L.M.: "Intensive care delirium. The effect of outside deprivation in a windowless unit", Arch Intern Med. 1972; 130(2), 225-226.

(Continued)

*Primary Examiner* — Thaddeus Cox

(57) ABSTRACT

The invention relates to a lighting system (100) and a method for controlling lighting conditions in a room (R). The lighting system (100) comprises a controller (101) for controlling internal light sources (121, 122) and at least one actuator (131, 141) for changing the amount of external light entering the room (R). Moreover, at least one sensor (111, 112, 31,141) is provided for detecting a parameter relating to the actual or to a desired lighting level of the room (R). Thus it is possible to control the lighting of the room (R) according to a predetermined schedule, particularly with a circadian rhythm that can reduce delirium in a patient (P). The actuator may for example comprise means (141) for closing or opening curtains (142) in front of a window (W).

16 Claims, 1 Drawing Sheet

(52) U.S. Cl.
CPC ..... *H05B 37/0218* (2013.01); *H05B 37/0245* (2013.01); *A61M 2021/0044* (2013.01); *A61M 2021/0083* (2013.01); *A61M 2205/3303* (2013.01); *A61M 2205/3306* (2013.01); *A61M 2205/502* (2013.01); *A61M 2205/52* (2013.01); *A61M 2230/63* (2013.01)

(58) Field of Classification Search
CPC .................. A61M 21/00; A61M 21/02; A61M 2021/0044; A61M 2021/0083
See application file for complete search history.

(56) References Cited

U.S. PATENT DOCUMENTS

| | | | |
|---|---|---|---|
| 2009/0182189 A1 | 7/2009 | Lira | |
| 2011/0010014 A1* | 1/2011 | Oexman | A47C 27/061 700/276 |
| 2012/0299486 A1* | 11/2012 | Birru | H05B 37/0218 315/153 |
| 2013/0085615 A1* | 4/2013 | Barker | A61G 10/00 700/277 |
| 2013/0165741 A1* | 6/2013 | Seabury | A61M 21/02 600/27 |

FOREIGN PATENT DOCUMENTS

| | | | |
|---|---|---|---|
| EP | 2003393 A1 | 12/2008 | |
| JP | 2005310438 A | 11/2005 | |
| JP | 2009224277 A | 10/2009 | |
| JP | 2009229370 A | 10/2009 | |
| JP | 2009259598 A | 11/2009 | |
| JP | 2010186700 A | 8/2010 | |
| JP | 2011510442 A | 3/2011 | |
| WO | 200188434 A1 | 11/2001 | |
| WO | 2004086195 A2 | 10/2004 | |
| WO | 2009044330 A1 | 4/2009 | |
| WO | WO 2010079388 A1 * | 7/2010 | ......... H05B 37/0245 |
| WO | 2011087681 A1 | 7/2011 | |
| WO | 2011098945 A1 | 8/2011 | |

OTHER PUBLICATIONS

Bramer, G.R. "International statistical classification of diseases and related health problems. Tenth revision", World health statistics quarterly, Rapport Trimestriel de Statistiques Sanitaires Mondiales, vol. 41, No. 1, p. 32, 1988.

Ely, E.W. "The impact of delirium in the intensive care unit on hospital length of stay", Intensive Care Med., Departments of Internal Medicine, Divisions of General Internal Medicine and Center for Health Services Research, Vanderbilt University Medical Center, Nashville, TN, 2001, 27, 1892-1900.

Maldonado, J.R.: "Delirium in the acute care setting: characteristics, diagnosis and treatment", Crit Care Clin, Department of Psychiatry, Stanford University School of Medicine, Stamford, CA 2008, 657-722.

Ely, E.W.. "Delirium as a predictor of mortality in mechanically ventilated patients in the intensive care unit", JAMA, 2004, 291(14): 1753-1762.

MacLullich, A.M. et al. "Delirium and long term cognitive impairment", Int. Rev. Psychiatry. 2009, 21(1): 30-42.

Guo, X., "Perioperative melatonin secretion in patients undergoing coronary artery bypass grafting". Anesth Analg, 2002, 94(5), 1085-91.

* cited by examiner

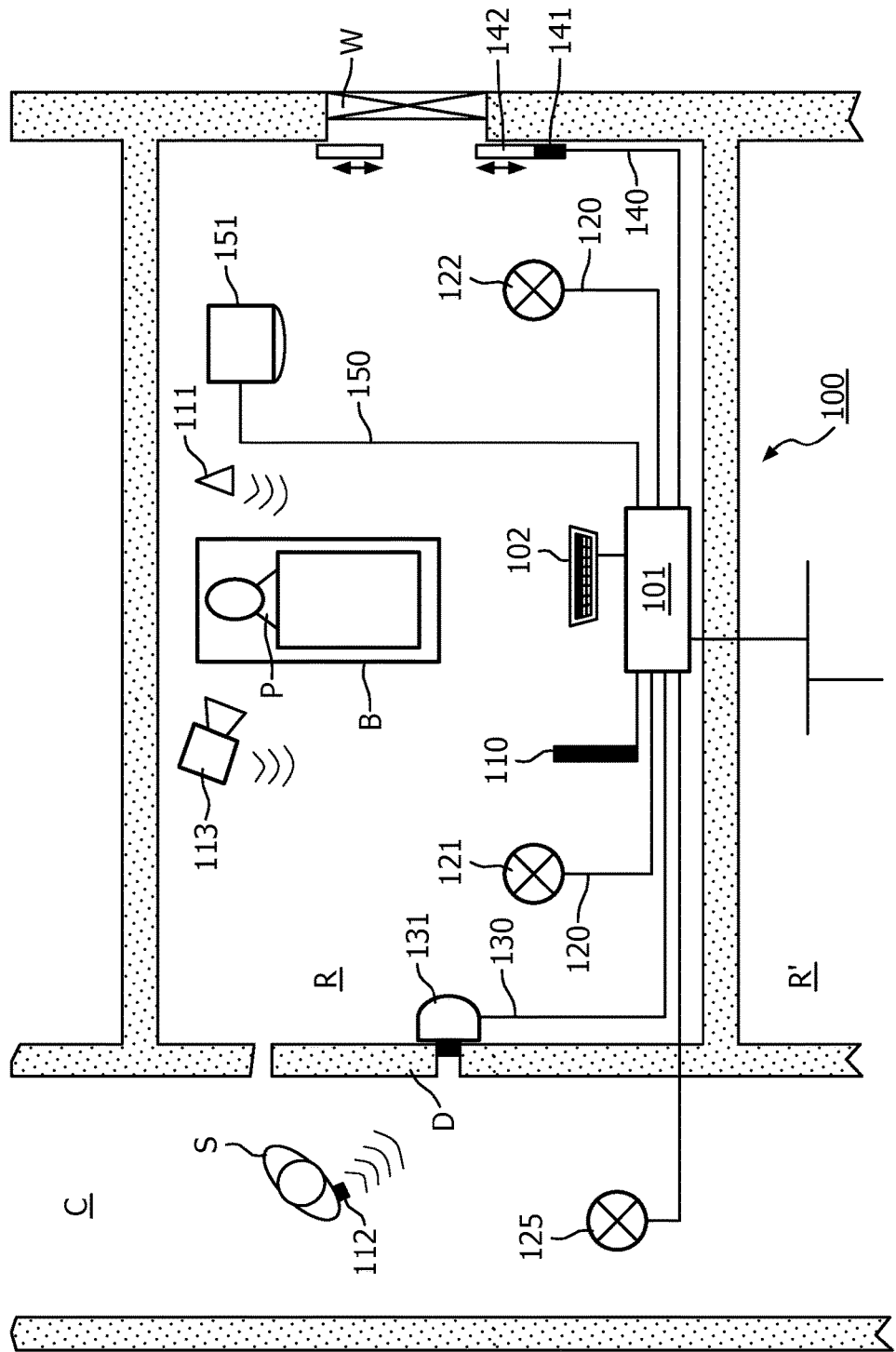

LIGHTING SYSTEM, PARTICULARLY FOR DELIRIUM REDUCTION IN INTENSIVE CARE UNITS

CROSS-REFERENCE TO PRIOR APPLICATIONS

This application is the U.S. National Phase application under 35 U.S.C. § 371 of International Application No. PCT/IB2013/053945, filed on May 15, 2013, which claims the benefit of U.S. Provisional Application No. 61/651,043, filed on May 24, 2012. This application is hereby incorporated by reference herein.

FIELD OF THE INVENTION

The invention relates to a lighting system and a method for controlling lighting conditions in a room, particularly in an intensive care unit.

BACKGROUND OF THE INVENTION

Delirium is an etiologically nonspecific organic cerebral syndrome characterized by concurrent disturbances of consciousness and attention, perception, thinking, memory, psychomotor behavior, emotion, and the sleep-wake schedule. Different studies suggest that a proper lighting environment for delirium reduction requires a circadian cycle of bright and dark periods that somewhat mimics the natural day and night cycle (Wilson, L. M.: "Intensive care delirium. The effect of outside deprivation in a windowless unit", Arch Intern Med, 1972, 130, 225-226; Guo, X., Kuzumi, E., Charman, S. C., and Vuylsteke, A.: "Perioperative melatonin secretion in patients undergoing coronary artery bypass grafting", Anesth Analg, Anaesthetic Research Unit, Papworth Hospital, Cambridge, UK., 2002, 94, 1085-91).

SUMMARY OF THE INVENTION

In view of the above, it would be desirable to have means that allow for a versatile control of lighting conditions in a room, particularly in an intensive care unit, wherein said lighting conditions should have a favorable effect on the health of a person or patient staying in the room.

This object is addressed by a lighting system according to claim 1, a method according to claim 2, a computer program product according to claim 13, a record carrier according to claim 14, and a usage according to claim 15. Preferred embodiments are disclosed in the dependent claims.

According to a first aspect, an embodiment of the invention relates to a lighting system for controlling lighting conditions in a room, for instance in an intensive care unit where a patient is housed, said room being called "controlled room" in the following. The lighting system comprises the following components:

At least one sensor for detecting a parameter that is related to the actual lighting level of the room or to a desired lighting level of the room.

At least one controllable light source that is or can be located in the room. For purposes of reference, this light source will in the following be called "internal light source".

At least one actuator for affecting the amount of external light entering the room.

A controller for controlling the internal light source and the actuator in dependence on the readings of the sensor, said readings indicating the value of the detected parameter. The controller may for example be realized by dedicated electronic hardware, digital data processing hardware with appropriate software, or a mixture of both.

The parameter that is detected by the sensor(s) may encode the actual or a desired lighting level in various ways, for example by a set of discrete levels (e.g. "dark", "dim", "normal", "bright"), or by values or ranges of values of appropriate physical units (e.g. lux).

The "external light" the entrance of which is controlled by the actuator originates by definition from a light source located outside the controlled room. This may for instance be an artificial light source such as a lamp in a neighboring room, or a natural light source (typically daylight).

It should be noted that all statements expressed for one sensor and/or one actuator are analogously valid for several sensors/actuators if the system comprises a plurality thereof.

According to a second aspect, the invention relates to a method for controlling lighting conditions in a room, said method comprising the following steps:

Detecting with at least one sensor a parameter related to the actual or to a desired lighting level of the room.

Controlling an internal light source and the amount of external light entering the room in dependence on the readings of said sensor.

The method comprises in general form the steps that can be executed with a lighting system of the kind described above. Explanations provided for the lighting system are therefore analogously valid for the method and vice versa.

The lighting system and the method have the advantage to allow for a versatile and accurate control of lighting conditions in a room by controlling both internal light sources and the entrance of external light in dependence on a measured and/or desired lighting level. Thus a close adherence to a desired lighting schedule can be guaranteed which is in many situations important for the health of a subject exposed to the light, for instance in an intensive care unit.

In the following, various preferred embodiments of the invention will be described in more detail that may be applied to refine both the lighting system and the method described above.

The sensor that is used to detect a parameter related to the actual or desired lighting level may optionally be a light sensor (or light meter) adapted to measure the actual light level prevailing at a particular location. It may for example be a light sensor that is or that can be located adjacent to a bed and/or that is or can be worn by a person (patient). In this case the light sensor can be used to detect actual lighting conditions of interest such as the amount of light a patient is exposed to. The light sensor may for instance be realized as a luxmeter or as a (video) camera.

In another embodiment, the sensor may be or comprise an activity sensor for detecting a state of activity of a patient. The activity sensor may preferably be adapted to allow for the detection of wakefulness and/or sleep of the patient. It may for instance be adapted to detect if the patient's eyes are closed (indicating a state of sleep), for example if the sensor comprises a camera-based device for monitoring the patient's face and appropriate image processing software to distinguish closed eyes from open eyes. Such a sensor will hence allow for a determination how much light is effectively "received" by the patient.

With the aforementioned activity sensor, the controller can be enabled to adapt its control of the internal light source(s) and/or of the actuator(s) to the activity of the patient. For example, if during a period in which bright light is desired the eyes of the patient are closed (because the patient is sleeping), the bright light period may be prolonged to compensate for that. Or, if for example during a period in which low light is desired the eyes of the patient are closed, the lights may more readily be turned up (e.g. if required by the staff) without a need to adjust the duration of the low light period.

Additionally or alternatively, the sensor(s) may be or comprise at least one door sensor for detecting the opening state of a door leading to the controlled room. Such a door sensor may for example be realized by a simple switch indicating just the two states "open" and "closed", or it may be a more versatile element such as a potentiometer which allows measuring the degree of opening of a door. Using a door sensor may provide valuable information about the possibility of external light entering through an open door.

In another embodiment, the sensor(s) may be or comprise at least one window sensor for detecting the light transmission capability of a window of the controlled room. If the window is for example provided with a curtain or blind, the window sensor may be designed to detect the opening state of this curtain/blind in a similar way as the above door sensor could detect the opening state of a door. If the window is provided with means such as an electrochromic device for controllably changing its light transmission capability, the window sensor may for example provide information about the control settings of this device (e.g. an applied voltage).

In still another embodiment, the sensor(s) may additionally or alternatively comprise at least one presence sensor for detecting the presence and/or the location of an object or a subject (person) in an area of surveillance, particularly within the controlled room. The presence sensor may optionally be a wirelessly operating tag that can be attached to or worn by the object/subject. Such a detector can for example be used to detect the presence of medical staff in a hospital room, indicating a situation where an increased lighting level is required.

In one embodiment of the invention, the actuator can be or comprise an actuator for changing the light transmission capability of a window. A window of the controlled room will usually allow for the entrance of varying amounts of ambient light from natural sources (e.g. the sun) or artificial sources (e.g. streets lights) that cannot be controlled from inside the room. With the described actuator, the amount of light entering the controlled room can however be regulated by adjusting the light transmission capabilities of the window appropriately.

The aforementioned actuator may for example comprise an actuator for actively closing or opening a curtain or blind. In another embodiment, the actuator may comprise a regulator for an electrochromic device with which the window is provided.

According to another embodiment of the invention, the actuator(s) may be or comprise a dimmer for a controllable light source located outside the controlled room, wherein said light source will in the following be called "external light source". The capability to control the emission level of external light sources allows for the prevention of disturbances by external light, particularly during times when a low lighting level is desired. Such disturbances may for instance occur when a door between the controlled room and a neighboring room or floor is opened. With the dimmer, the external light source(s) can be turned down during such times.

The internal light source may typically comprise one or more lamps that are used for the complete illumination of the controlled room. It may however also be or comprise at least one other light source that is not (or at least not primarily) intended for illuminating the room but which nevertheless contributes to the prevailing lighting level. Such a light source may for instance be a display of a patient monitoring device or of a television apparatus. Controlling the light emission of such subordinate light sources allows for a very precise adherence to desired lighting conditions.

The lighting system may further preferably comprise a user interface such as a keyboard or a touch pad allowing for the input of information by a user. Thus the desired lighting schedule can readily be selected and adjusted.

In another embodiment of the invention, at least one source of sound is provided (e.g. as a further component of the lighting system), wherein said source of sound is or can be controlled by the controller. Thus not only the lighting level but also the noise level within the room can be controlled, allowing for a synchronized realization of periods of rest (low lighting level and silence) and activity, respectively.

In general, the light level within the controlled room may be controlled according to any schedule or target behavior that is desired for the application at hand. In a preferred embodiment, the internal light source(s) and/or the actuator(s) is/are controlled according to a predetermined time schedule having a circadian cycle of dark and light periods. Thus the physiological and/or mental state of a biological subject (patient, animal etc.) staying in the controlled room can favorably be affected.

In the aforementioned embodiment, the dark period may for instance last for at least 5 hours a day, for at least 6 hours a day, for at least 7 hours a day, or preferably for at least 8 hours a day. Additionally or alternatively, the bright period may last for at least 3 hours a day, for at least 4 hours a day, for at least 5 hours a day, or preferably for at least 6 hours a day.

In many situations the illumination of the controlled room is composed of contributions from internal light sources and external light sources. In a preferred embodiment, the lighting conditions in the room are controlled such that these contributions can be adjusted according to a given priority setting. For example, if natural lighting is preferred, the (artificial) internal light source(s) may be switched on only as much as necessary to supplement external daylight in achieving a desired light level.

The described method and/or the desired behavior of the lighting system will typically be realized with the help of a computing device, e.g. a microprocessor or an FPGA in the controller of the lighting system. Accordingly, the present invention further includes a computer program product which provides the functionality of any of the methods according to the present invention when executed on a computing device.

Further, the present invention includes a data carrier, for example a floppy disk, a hard disk, an EPROM, a compact disc (CD-ROM), a digital versatile disc (DVD), or a USB stick which stores the computer product in a machine readable form and which executes at least one of the methods of the invention when the program stored on the data carrier is executed on a computing device. The data carrier may particularly be suited for storing the program of the computing device mentioned in the previous paragraph.

Nowadays, such software is often offered on the Internet or a company Intranet for download, hence the present invention also includes transmitting the computer product according to the present invention over a local or wide area network.

The invention further relates to the usage of the lighting system described above for affecting a circadian rhythm of a subject, particularly for a treatment of delirium, sleeping disorder, and/or jetlag.

BRIEF DESCRIPTION OF THE DRAWINGS

These and other aspects of the invention will be apparent from and elucidated with reference to the embodiments described hereinafter.

In the drawings:

FIG. 1 schematically shows a top view of an intensive care unit that is provided with a lighting system according to an embodiment of the present invention.

DETAILED DESCRIPTION OF EMBODIMENTS

Delirium is an etiologically nonspecific organic cerebral syndrome characterized by concurrent disturbances of consciousness and attention, perception, thinking, memory, psychomotor behavior, emotion and the sleep-wake schedule (G. Brämer: "International statistical classification of diseases and related health problems. Tenth revision", World health statistics quarterly, Rapport trimestriel de statistiques sanitaires mondiales, vol. 41, no. 1, p. 32, 1988). It is a state of confusion whose intensity may rapidly fluctuate over time.

The exact cause of delirium is currently unknown and it is likely to be multiple. It is a quite prevalent condition in intensive care units (ICUs) with rates normally reported to be two digits high in different studies (Ely, E. W., Gautam, S., Margolin, R., Francis, J., May, L., Speroff, T., Truman, B., Dittus, R., Bernard, R., and Inouye, S. K.: "The impact of delirium in the intensive care unit on hospital length of stay", Intensive Care Med, Departments of Internal Medicine, Divisions of General Internal Medicine and Center for Health Services Research, Vanderbilt University Medical Center, Nashville, Tenn. 37232-8300, USA, 2001, 27, 1892-1900; Maldonado, J. R.: "Delirium in the acute care setting: characteristics, diagnosis and treatment", Crit Care Clin, Department of Psychiatry, Stanford University School of Medicine, Stanford, Calif. 94305, USA, 2008, 24, 657-722, vii). Whatever the cause of delirium, it represents a burden for patients who report terrifying hallucinations and for the hospital staff who has to cope with uncooperative and irrational behavior. Furthermore, delirium has been reported to be linked with a series of negative outcomes for patients and society.

Patients who develop delirium are more likely to stay longer in the hospital and die earlier in comparison to patients who do not develop the condition (Ely, E. W., Shintani, A., Truman, B., Speroff, T., Gordon, S. M., Harrell, F. E., Inouye, S. K., Bernard, G. R., and Dittus, R. S.: "Delirium as a predictor of mortality in mechanically ventilated patients in the intensive care unit", JAMA, Department of Medicine, Division of General Internal Medicine and Center for Health Services Research and the Veterans Affairs Tennessee Valley Geriatric Research, Education and Clinical Center, Nashville, Tenn., USA., 2004, 291, 1753-1762). Surviving patients who experienced delirium are also at a greater risk of developing long term cognitive impairments (MacLullich, A. M. J., Beaglehole, A., Hall, R. J., and Meagher, D. J.: "Delirium and long-term cognitive impairment", Int Rev Psychiatry, icine, University of Edinburgh, Royal Infirmary of Edinburgh, Edinburgh, Scotland, UK, 2009, 21, 30-42). All in all, delirium is a serious problem that deserves attention due to its high prevalence and negative associations.

Despite its prevalence and potential negative consequences there is currently no specific treatment for delirium and interventions are addressed mainly to control the symptoms once the condition is manifested. In this context prevention can be regarded as the most important strategy for addressing delirium amongst ICU patients. Effective prevention requires however the identification of causes or at least of precipitating factors of ICU delirium. Among these factors there is a body of evidence suggesting that lighting conditions in the patient's environment affect the odds of delirium in the ICU population.

Different studies suggest that a proper lighting for delirium reduction requires a circadian cycle of bright and dark periods that somewhat mimics the natural day and night cycle. In a hospital environment, humans may however disrupt the light cycle in many discretionary ways: during the night, nurses turn on the light for examination or bedside lamps are used for reading; during the day curtains are regulated by people and might create a dark environment. Display monitors of electronic equipment (e.g., TVs, medical equipment) in the room may also contribute to increasing the ambient light level to a magnitude higher than desired during the night.

Given the available evidence that a circadian cycle of bright and dark periods reduces delirium rates in intensive care units, it is important to expose patients to illumination contrasts within a somewhat pre-determined schedule. When doing this by a system that controls ambient therapeutic light automatically, a balance between staff needs and patient needs, and the therapeutic effects of lighting should be achieved, while allowing for modifications by staff and patient whenever needed.

In the following, embodiments of a system and a method of controlling lighting sources in intensive care units (or other facilities) are described that are intended for, among other things, achieving these purposes and particularly for reducing delirium rates.

A lighting system according to an embodiment of the invention serves for controlling, documenting and/or reporting the sources of lighting in a room, such system being comprised of one or more of the following components:

one or more artificial lighting sources in the room and immediately outside the room (e.g., corridor or adjacent room);

automated window curtains or blinds, or electrochromic devices (also known as "smart glass");

a light sensor or set of light sensors configured for sensing the intensity of light in the room from sources external to the room, e.g., entering the room via one or more windows, or one or more doors or via other openings, with or without transparent or translucent barriers;

a door sensor or set of door sensors configured for sensing whether a room's door is open or closed;

a control system with a controller configured for controlling the artificial light sources, and the curtains, blinds and/or electrochromic devices for adjusting a light level or light intensity in the room or in a part of the room according to a pre-determined time schedule and in response to the sensor signals from the light sensor(s) and/or the door sensor(s); the control system may be implemented, for example, by means of dedicated control software running on a computer, dedicated hardware or a combination thereof;

a user interface that allows changes in the manner wherein the control system controls the artificial light sources, and the curtains and/or blinds and/or electrochromic devices (i.e., the user-interface allows an operator of the control system such as the patient him/herself or a member of the hospital staff, making changes to the controller settings);

An embodiment of a method for controlling the aforementioned lighting system may comprise at least one of the following steps:

setting the room's lighting to a bright level for at least 6 hours of the day by combined control of the lighting sources and window curtains/blinds/electrochromic devices under control of the sensor signals;

setting the room's lighting to dark level for at least 8 hours of the day by combined control of the lighting sources and window curtains/blinds/electrochromic devices under control of the sensor signals;

automatically repeating the settings above in regular intervals of 24 hours;

allowing for temporary overriding of the above settings by patients and/or staff.

FIG. 1 schematically sketches in embodiment of a lighting system 100 of the kind explained above which is installed in a hospital room R such as an intensive care unit (ICU).

As a central component, the lighting system 100 comprises a controller 101 which may be realized by digital data processing units such as a microprocessor or a personal computer. The controller 101 may be located (as shown) inside the controlled room R or at any other convenient location from where it can be connected (by wire and/or wirelessly) to the controlled components. A user interface 102 is preferably connected to the controller 101 to allow for user inputs. It may for example be realized by a keyboard, a touch screen, physical knobs or buttons or rotary dials.

The lighting system 100 further comprises one or more internal light sources such as lamps 121, 122 that are disposed inside the controlled room R and adapted to (completely) illuminate it. The lamps may for example comprise full spectrum fluorescent lamps that are able to deliver a range of light intensities to the subject eyes. The internal light sources 121, 122 are connected to the controller 101 by control lines 120 via which the controller can adjust their brightness (and optionally other parameters such as their color). This adjustment is preferably possible continuously or in steps from 0% (shut-off) to 100% of the maximal brightness.

It should be noted that all connections between the controller 101 and other components of the lighting system 100 may be realized by wire or wirelessly, irrespective of the specific manner they are illustrated in the FIGURE.

The lighting system 100 further comprises an optional door sensor and actuator 131 that is connected to the controller 101 via a door control line 130. The door sensor and actuator 131 allows for detecting the opening state of a door D leading to the room R. Moreover, it preferably further allows for an active closing and/or opening of the door D according to some internal timer and/or under control of the controller 101.

The controller 101 is further connected to an external light source, for example a lamp 125 in the corridor C adjacent to the patient room R. This allows for an additional control of light from external sources that may affect the prevailing lighting level in the room.

The above mentioned door sensor and actuator 131 and the controllable external light source 125 are preferably used in combination by the controller 101. For example, during periods in which low light levels are required in the room R, the light in the corridor C may automatically be dimmed (e.g. with a dimmer integrated into the external lamp 125 or the controller 101) every time the door D is open so as not to violate the specified schedule. Upon closing of the room's door, the corridor light may return to normal levels. Moreover, the door should automatically close in order to reduce illumination disruptions.

The lighting system 100 further comprises an optional window sensor and actuator 141 for moving curtains 142 of a window W of the patient room R. The window sensor and actuator 141 is connected to the controller 101 via a window control line 140 and may be used to determine and/or affect the amount of external light (e.g. daylight) entering the room R through the window W. The optional sensing capability of this device may be able to provide a signal indicative of the opening state of the curtain and/or the amount of external light entering through the window. Instead of a curtain 142, other elements such as a blind, a shutter, or an electrochromic device might be used to control the (effective) light transmission capability of the window. Moreover, the window that is shown here as an external window of the building might also be located towards a neighboring room such as a corridor or a control room.

Furthermore, the lighting system 100 comprises a light sensor 111 which may preferably be located near the patient eyes and which may be wearable (i.e., worn by the patient P) or placed in the patient's surroundings (e.g. bed B, wall, etc.). Examples of such light sensors include luxmeters (measuring illuminance), or video cameras. In the shown embodiment, the light sensor 111 is adapted to communicate wirelessly with an antenna 110 of the controller 101. The light sensor 111 can be used to measure the actual lighting level at the position of the patient P or close thereto and to communicate an associated parameter to the controller 101. The signal of the light sensor 111 can be processed by the controller 101 in order to 'smooth' variations in the measurements. Depending on the transmitted parameter, the controller can adjust the various actuators it is connected to in order to guarantee the adherence to a desired lighting schedule. The controller can for example address the internal light sources 121, 122 and the external light source 125 for regulating their emission, the window actuator 141 for closing or opening the curtains, and/or the door actuator 131 for closing the door.

The FIGURE further shows an (optional) "activity sensor" 113 that measures how much light is actually "received" by the patient P. This sensor could be e.g. a camera-based device detecting whether the eyes of the patient are open or closed. Based on that information, the lighting schedule may be adapted. For example if during the period in which bright light is desired the eyes of the patient are closed (because the patient is sleeping), the bright light period may be prolonged to compensate for that.

If the aforementioned activity sensor 113 is something like a camera-based device, it may additionally fulfill the function of the light sensor 111. However, it is also possible that the activity sensor may be realized in other ways, for example as a sensor for detecting parameters such as heart rate and/or brain activity of the patient that allow for the determination of the patient's state of activity (e.g. wakefulness or sleep).

It should be noted that, while the door sensor and actuator 131 is shown as an integrated device, it may also be realized by a physically separate sensor and detector. The same applies to the window sensor and actuator 141.

During operation of the lighting system 100, the timing, duration and intensity of illumination are set by the controller 101 that stores and executes an associated lighting schedule. This schedule may for example primarily define a fixed amount of time and intensity in which the light sources remain on. The settings of this schedule are preferably modifiable via the user interface 102. A default schedule may be set according to the following exemplary table:

| Time | Light intensity near patient eyes (lux) |
| --- | --- |
| 22:00 h-6:00 h | <10 lux |
| 6:00 h-8:00 h | unspecified |
| 8:00 h-14:00 h | >1000 lux |
| 14:00 h-22:00 h | unspecified |

Unspecified portions of the schedule can assume any value at the discretion of patients or staff. At any point, the staff or patient may override the scheduling, e.g., by pressing on or more switches in the room R for control of a lighting source 121, 122 or the window curtain 142 (or blinds or electrochromic device). Each switch may be associated with a timer so that lighting conditions return to the normal (default) schedule after a fixed interval of time.

In order to better enforce the desired schedule, the controller 101 can actuate the window curtains 142 (or any equivalent control device for the window's transmission capability) based on the sensor signal from the light sensor 111 located near the patient eyes and windows and/or from the activity sensor 113. Preferences can optionally be set at the controller 101 for the desired primary source of light (artificial or natural) associated with this light sensor.

In the shown embodiment of the lighting system 100, the intensity of light sources in the equipment used for patient monitoring is also actuated by the controller 101 in order to better ensure schedule compliance. During periods in which low light levels are required, the light in the monitoring equipment 151 is automatically dimmed. When bright light levels are required, the lighting of monitors 151 can be enhanced to improve readability by staff.

Additionally or alternatively, the intensity of light sources in the equipment used for patient monitoring may be increased when the presence of staff is detected in the room R. Presence detection may for example be accomplished with PIR (Passive Infra Red) sensors, video cameras, RFID (Radio-frequency Identification) or other enabling technology. In the described embodiment, members S of the staff are shown to wear RFID tags 112 that can communicate wirelessly with the controller 101. If, after the staff has left the room R, the presence has not been detected for a certain amount of time, the intensity of light sources 151 in the monitoring equipment may return to normal levels or may even be set to zero (shut off) during periods in which low light levels are desired.

In another embodiment, the sound levels of e.g. alarms in the equipment used for patient monitoring may also be actuated by the controller 101. During periods in which low light levels are required, the sound level in monitoring equipment may automatically be dimmed. When bright light levels are required, the sound level of monitors or other equipment can be increased.

The FIGURE also indicates the possibility that the lighting system 100 can span multiple rooms R, R', . . . via a network, or bus, for connecting the controller 101, the light sensors, the door sensors and associated actuators (for closing the doors), the lighting sources, the window curtains/blinds/electrochomic devices, and other optional components.

In summary, an embodiment of a lighting system and a method for controlling lighting conditions in a room R has been described wherein the lighting system 100 comprises a controller 101 for controlling internal light sources 121, 122 and at least one actuator 131, 141 for changing the amount of external light entering the room R. Moreover, at least one sensor 111, 112, 113, 131, 141 is provided for detecting a parameter relating to the actual or to a desired lighting level of the room R. Thus it is possible to control the lighting of the room R according to a predetermined schedule, particularly with a circadian rhythm that can reduce delirium in a patient P. The actuator may optionally comprise means 141 for closing or opening curtains 142 in front of a window W.

The lighting system and the method are particularly suitable for hospitals as a building block of healing environments. Nevertheless, they may be useful in others areas in which influencing the circadian rhythm is desirable such as reducing the jetlag of intercontinental travelers in hotel rooms and correcting sleep disorders at home.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A lighting system for controlling lighting conditions in a room for affecting a circadian rhythm of a person in the room, comprising:
   at least one sensor for detecting a parameter relating to an actual lighting level of the room or to a desired lighting level of the room;
   at least one controllable internal light source that is or can be located in the room;
   a controllable external light source located outside the room;
   a door sensor for detecting an opening state of a door of the room;
   at least one actuator for affecting an amount of external light entering the room through the door;
   a controller configured to control the internal light source, the controllable external light source, and the actuator in dependence on both i) readings of the sensor and ii) a predetermined lighting schedule, to establish lighting conditions in the room, said predetermined lighting schedule having a circadian cycle of alternating dark period and bright period, wherein, when the room is under a low light level according to the predetermined lighting schedule and the door sensor detects an opening of the door, the controllable external light source is automatically dimmed.

2. The lighting system according to claim 1 further comprising:
an activity sensor for detecting a state of activity of the person; wherein
said controller is configured to control the lighting schedule to said state of activity.

3. The lighting system according to claim 2, wherein:
the state of activity is characterized in that the person's eyes are closed; and
said controller is configured to prolong the bright period to compensate for the person's eyes being closed during the bright period.

4. The lighting system according to claim 1, wherein the sensor comprises at least one sensor selected from the group consisting of:
a light sensor that is or can be located adjacent to a bed and/or that can be worn by a patient;
a window sensor for detecting light transmission capability of a window;
a presence sensor for detecting presence and/or location of an object or a person.

5. The lighting system according to claim 1, wherein the actuator comprises:
an actuator for changing light transmission capability of a window;
an actuator for closing or opening a curtain or blind;
a regulator for an electrochromic device; or
a dimmer for the controllable external light source.

6. The lighting system according to claim 1, wherein the internal light source comprises a lamp and/or a display.

7. The lighting system according to claim 1, further comprising a user interface.

8. The lighting system according to claim 1, wherein the dark period last for at least seven hours a day and/or the bright period last for at least five hours a day.

9. The lighting system according to claim 1, wherein contributions of the internal light source and of external light are adjusted according to given priority settings.

10. A hospital room comprising the lighting system according to claim 1.

11. An intensive care unit in a hospital comprising the lighting system according to claim 1.

12. The lighting system according to claim 1, wherein:
the state of the door includes a degree of opening of the door.

13. The lighting system according to claim 1, wherein:
the at least one actuator is configured to automatically effectuate closing of the door upon detection of the opening of the door; and
the controller is configured to control the controllable external light source to return to a normal level upon closing of the door.

14. A method for controlling lighting conditions in a room for affecting a circadian rhythm of a person in the room, said method comprising the following steps:
providing at least one controllable internal light source that is or can be located in the room, a controllable external light source located outside the room, and at least one actuator for affecting an amount of external light entering the room;
detecting an opening state of a door of the room by a door sensor;
detecting with at least one sensor a parameter relating to an actual lighting level of the room or to a desired lighting level of the room;
controlling the internal light source, the controllable external light source, and the actuator in dependence on both i) readings of the sensor and ii) a predetermined lighting schedule, to establish lighting conditions in the room, said predetermined lighting schedule having a circadian cycle of alternating dark period and bright period,
wherein, when the room is under a low light level according to the predetermined lighting schedule and the door sensor detects an opening of the door, the controllable external light source is automatically dimmed.

15. The method according to claim 14, further comprising controlling the internal light source and the amount of external light for treating delirium in a patient.

16. A lighting system for controlling lighting conditions in a hospital room, comprising:
at least one sensor for detecting a parameter relating to an actual lighting level of the room or to a desired lighting level of the hospital room;
at least one controllable internal light source located in the hospital room;
a controllable external light source located outside the room;
a door sensor for detecting an opening state of a door of the room;
at least one actuator for affecting an amount of external light entering the hospital room;
a controller configured to control the internal light source, the controllable external light source, and the actuator in dependence on both i) readings of the sensor and ii) a predetermined lighting schedule, to establish lighting conditions in the hospital room, said predetermined lighting schedule having a circadian cycle of alternating dark period and bright period,
wherein said controller is further configured to:
set the lighting conditions in the hospital room to a bright level for at least 6 hours of a day by combined control of the internal light source and the actuator,
set the lighting conditions in the hospital room to a dark level for at least 8 hours of a day by combined control of the internal light source and the actuator,
automatically repeat said bright level settings and said dark level settings in regular intervals of 24 hours, and
allow for temporary overriding of said bright level settings and said dark level settings by a person in the hospital room,
when the room is under a low light level according to the predetermined lighting schedule and the door sensor detects an opening of the door, automatically dim the controllable external light source.

* * * * *